(12) United States Patent
Simmons et al.

(10) Patent No.: US 9,795,680 B2
(45) Date of Patent: Oct. 24, 2017

(54) PHARMACEUTICAL COMPOSITIONS FOR TREATING EAR DISEASES

(71) Applicant: Professional Compounding Centers of America (PCCA), Houston, TX (US)

(72) Inventors: Chris V. Simmons, Sugar Land, TX (US); Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 169 days.

(21) Appl. No.: 14/831,590

(22) Filed: Aug. 20, 2015

(65) Prior Publication Data

US 2016/0051686 A1    Feb. 25, 2016

Related U.S. Application Data

(60) Provisional application No. 62/039,794, filed on Aug. 20, 2014.

(51) Int. Cl.

| | | |
|---|---|---|
| A61K 36/00 | (2006.01) | |
| A61K 47/44 | (2017.01) | |
| A61K 9/00 | (2006.01) | |
| A61K 45/06 | (2006.01) | |
| A61K 36/48 | (2006.01) | |
| A61K 47/34 | (2017.01) | |
| A61K 31/685 | (2006.01) | |
| A61K 31/695 | (2006.01) | |
| A61K 36/889 | (2006.01) | |
| A61K 36/47 | (2006.01) | |

(52) U.S. Cl.
CPC .......... *A61K 47/44* (2013.01); *A61K 9/0046* (2013.01); *A61K 31/685* (2013.01); *A61K 31/695* (2013.01); *A61K 36/47* (2013.01); *A61K 36/48* (2013.01); *A61K 36/889* (2013.01); *A61K 45/06* (2013.01); *A61K 47/34* (2013.01)

(58) Field of Classification Search
None
See application file for complete search history.

*Primary Examiner* — Qiuwen Mi
(74) *Attorney, Agent, or Firm* — David G. Woodral; Scott R. Zingerman; Gable Gotwals

(57) ABSTRACT

The present disclosure relates to pharmaceutical compositions with increased skin permeability for treating ear disease in mammals. Disclosed pharmaceutical compositions are prepared as topical gels or as transdermal gels. The pharmaceutical compositions reduce ear inflammation and irritation produced by ear diseases or injuries (e.g., cauliflower ear, chronic otitis, and the like). The pharmaceutical compositions include a synergistic combination of pracaxi oil and seje oil. Additionally, the pharmaceutical compositions include phosphatidylcholine as a permeation enhancer. The combination of aforementioned natural components exhibits enhanced healing properties, thereby providing organic acids with antioxidant, antibacterial, and antifungal properties. The synergistic combination of pracaxi and seje oil increases the skin permeability to active pharmaceutical ingredients (APIs), thereby passing through the stratum corneum and reaching the target area; therefore, the dosage and time of treatment is significantly reduced.

12 Claims, 2 Drawing Sheets

PHARMACEUTICAL COMPOSITIONS FOR TREATING EAR DISEASES

CROSS-REFERENCE TO RELATED APPLICATIONS

This application claims priority to U.S. Provisional Application Ser. No. 62/039,794, filed Aug. 20, 2014, which is hereby incorporated by reference.

BACKGROUND

Field of the Disclosure

The present disclosure relates generally to pharmaceutical compositions, and more particularly, to pharmaceutical compositions natural components for treating ear diseases.

Background Information

An example of an ear disease is cauliflower ear, which is a deformity of the ear that results from an untreated aural hematoma. The fluid-filled swelling of the hematoma is often caused by chronic allergies and ear infections, and becomes firm and thickened over time, thus resulting in the cauliflower ear. Ear infections may lead to hematomas. Hematomas in the earflaps (aural hematomas) cause swelling that is created by a broken blood vessel after bleeding has occurred inside a tissue.

The cartilage of the ear has no other blood supply except that supplied by the overlying skin. When the skin is pulled from the cartilage and/or separated from the cartilage by blood (as with accumulated blood from injury or inflammation or infection), the cartilage is deprived of important nutrients. Ultimately, the cartilage dies and the risk of infection is increased. Additionally, an untreated ear infection leads to head shaking of the affected subject that breaks blood vessels within the earflap. An aural hematoma occurs when the blood accumulates within the cartilage layers of the ear. The earflap may partially or completely swell with the blood vessel and block off the ear canal; therefore, the earflap feels fluid-filled. Hematomas in the earflaps are found not only in humans but also in animals (e.g., in dogs with long, floppy ears). Generally, in mammals, hematomas do not heal without treatment.

Treatment of ear hematomas in mammals begins by identifying and treating the underlying condition that promoted the swelling (e.g., ear infection or the presence of mites). A conventional technique employed to reduce the hematoma is the needle aspiration. A drawback of employing aforementioned procedure is that the hematoma usually re-forms. Therefore, the veterinarian usually performs surgery on the ear to ensure the hematoma does not come back. The surgery generally involves making an S-shaped incision on the surface of the ear, and flushing out the blood and clots that caused the swelling. Common treatments for ear diseases include topical or transdermal compositions with active pharmaceutical ingredients (APIs) that are in contact with the swollen or infected tissue, but these topical or transdermal compositions cause irritation on the ear tissue. Conventional topical or transdermal compositions for ear diseases require long treatment periods of about 6 months to a year in order to see improvement of the ear condition.

Additionally, cartilage damage may result from piercing the upper ear in the cartilage. Piercing can lead to a type of ear cartilage infection called auricular perichondritis, which can result in cauliflower ear. Another cause of cauliflower ear results from the inflammation of ear cartilage in relapsing polychondritis.

FIG. 1 is a graphical representation illustrating a canine ear anatomy. In FIG. 1, canine ear anatomy 100 includes vertical canal 102, horizontal canal 104, and tympanic membrane 106. Canines have very unique ear anatomy and ear canals are difficult to treat because of its shape. Vertical canal 102 takes a short turn in order to end up in horizontal canal 104; and horizontal canal 104 ends up in tympanic membrane 106. The average volume of a dog's ear canal is generally filled with about 1.5 mL. Conventional otic preparations generally have a dosage of about 4 to 6 drops, or about 6 to 10 drops once or twice a day; therefore, since about 20 drops are needed to make one mL, dosages of 10 drops or less are not enough to fill the vertical canal 102 or the horizontal canal 104 of a dog. Consequently, there is a need for delivering the right amount of otic compositions needed to fill in the ear canals. Furthermore, some animals tend to shake out the otic composition from their ear after the otic composition has been delivered; therefore, the treatment may not be effective.

SUMMARY

The present disclosure relates to pharmaceutical compositions with increased skin permeability for treating ear diseases in mammals. In some embodiments the pharmaceutical compositions are topical gels. In other embodiments, the pharmaceutical compositions are transdermal gels. In these embodiments, the pharmaceutical compositions reduce ear inflammation and irritation produced by ear diseases or injuries (e.g., cauliflower ear, chronic otitis, and the like). In further embodiments, the pharmaceutical compositions decrease the inflammation and irritation of the outer ear; therefore, the elasticity of affected tissue is improved, thereby gaining access to the site of the infection within the middle or inner ear.

In some embodiments, the pharmaceutical compositions include natural components from the Amazon forest. In these embodiments, the pharmaceutical compositions include pracaxi oil and seje oil. Further to these embodiments, aforementioned natural components exhibit enhanced healing properties, thereby providing organic acids with antioxidant, antibacterial, and antifungal properties.

In some embodiments, the pharmaceutical compositions include a synergistic combination of pracaxi oil and seje oil. In these embodiments, the pharmaceutical compositions include phosphatidylcholine as a permeation enhancer.

In an example, the pharmaceutical compositions include: pracaxi oil in amounts ranging from about 0.5% w/w to about 15% w/w, preferably from about 1% w/w to about 5% w/w; seje oil in amounts ranging from about 0.5% w/w to about 15% w/w, preferably from about 1% w/w to about 5% w/w; phosphatidylcholine in amounts ranging from about 0.1% w/w to about 5% w/w, preferably from about 0.5% w/w to about 2% w/w; and silicone in amounts ranging from about 10% w/w to about 95% w/w, preferably from about 10% w/w to about 50% w/w.

In other embodiments, the pharmaceutical compositions include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. Further to these embodiments, the concentration of each natural component within pharmaceutical compositions is from about 1% w/w to 20% w/w, more preferably about 5% w/w.

In further embodiments, the pharmaceutical compositions can be applied alone or as a carrier for APIs (e.g., antibiotics, anti-fungal, cortical steroids, non-steroidal anti-inflammatories, anti-parasites, and the like).

In some embodiments, when an affected area is not reachable because of the inflammation caused by ear diseases, the application of disclosed pharmaceutical compositions reduces the inflammation and opens up the ear canal to enable for other pharmaceutical compositions including any suitable APIs or the pharmaceutical compositions by themselves to be applied directly into the affected area.

In some embodiments, the amounts of the natural components within the pharmaceutical compositions are combined to produce a single dosage form. In these embodiments, the pharmaceutical composition dosage forms include: sprays, ointments, pastes, creams, lotions, solutions, topical gels, patches, among others. In these embodiments, the pharmaceutical compositions enable for continuous treatment of ear diseases by applying one layer of disclosed pharmaceutical compositions into the affected area of a patient.

In some embodiments, various additives are included to facilitate the preparation of suitable dosage forms. For example, additives include gelling agents, thickening agents, pH adjusters, preservatives, colors, stabilizing agents, antioxidants, and surfactants, among others.

Numerous other aspects, features of the present disclosure may be made apparent from the following detailed description, taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Figure 1:
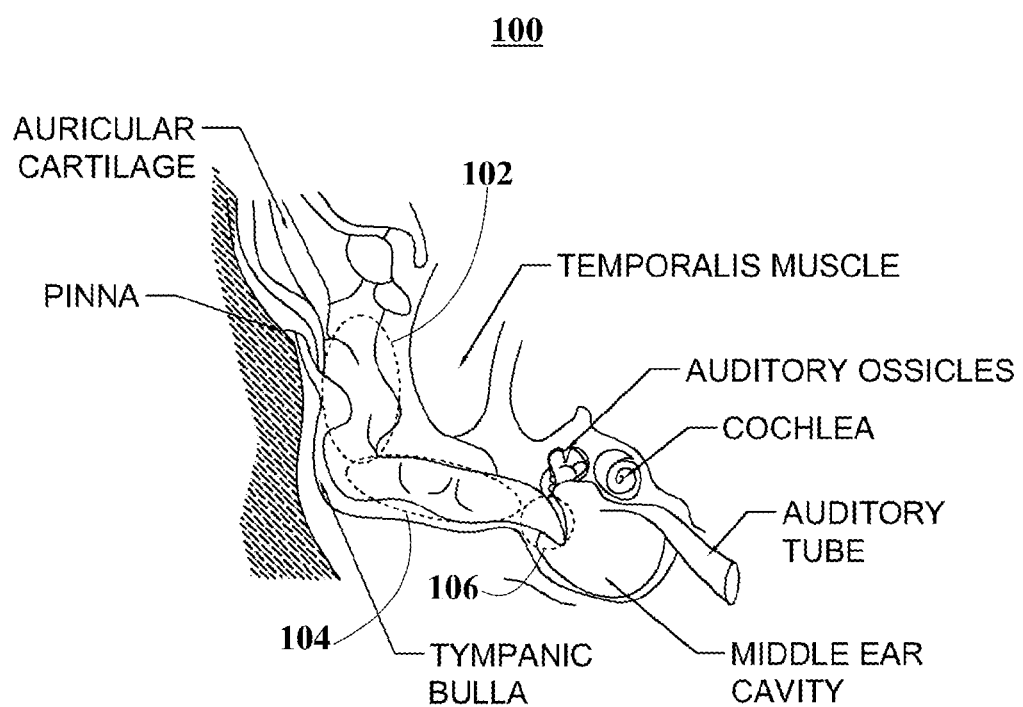
FIG. 1 is a graphical representation illustrating a canine ear anatomy, according to an embodiment.

The present disclosure is here described in detail with reference to embodiments, which form a part here. Other embodiments may be used and/or other changes may be made without departing from the spirit or scope of the present disclosure. The illustrative embodiments described in the detailed description are not meant to be limiting of the subject matter presented here.

Definitions

As used here, the following terms have the following definitions:

"Active Pharmaceutical Ingredients (APIs)" refer to chemical compounds that induce a desired effect, and include agents that are therapeutically, prophylactically, or cosmeceutical effective.

"Gel" refers to a colloid in which the solid disperse phase forms a network in combination with that of the fluid continuous phase, thus resulting in a viscous semi-rigid solution.

"Liposomes" refer to spherical, self-enclosed vesicles composed of amphipathic lipids.

"Permeation enhancement" refers to an increase in the permeability of the skin or mucosal tissue to the selected active pharmaceutical ingredients.

"Silicone" refers to polymeric organic silicon compounds obtained as oils.

"Topical administration" refers to delivery of a topical drug or active pharmaceutical ingredient to the skin or mucosa, thus providing a local effect.

"Transdermal pharmaceutical composition" refers to topical medications that may be used in different application forms, such as for example patches, ointments, creams, lotions, pastes, gels, and the like, and which release one or more active drugs through the stratum corneum at a predetermined rate over a defined period of time to a defined site of application.

"Treating" or "Treatment" refers to reduction in severity and/or frequency of symptoms, elimination of symptoms and/or underlying cause, prevention of the occurrence of symptoms and/or their underlying cause, and improvement or remediation of damage.

DESCRIPTION OF THE DISCLOSURE

The present disclosure relates to pharmaceutical compositions with increased skin permeability for treating ear diseases in mammals. In some embodiments the pharmaceutical compositions are topical gels. In other embodiments, the pharmaceutical compositions are transdermal gels. In these embodiments, the pharmaceutical compositions reduce ear inflammation and irritation produced by ear diseases or injuries (e.g., cauliflower ear, chronic otitis, and the like). These aforementioned injuries lead to changes in the epithelial tissues of the outer ear, thereby changing the physiologic appearance and causing irritation. In further embodiments, the pharmaceutical compositions decrease the inflammation and irritation of the outer ear; therefore, the elasticity of affected tissue is improved, thereby gaining access to the site of the infection within the middle or inner ear.

Formulation

In some embodiments, the pharmaceutical compositions include natural components from the Amazon forest. In these embodiments, the pharmaceutical compositions include pracaxi oil and seje oil. Further to these embodiments, aforementioned natural components exhibit enhanced healing properties, thereby providing organic acids with antioxidant, antibacterial, and antifungal properties.

In some embodiments, the pharmaceutical compositions include a synergistic combination of pracaxi oil and seje oil. In these embodiments, the pharmaceutical compositions include phosphatidylcholine as a permeation enhancer. In other embodiments, the pharmaceutical compositions including natural components increase the penetration of active pharmaceutical ingredients (APIs) through the skin. In these embodiments, the pharmaceutical compositions are safe and effective. In these embodiments, the aforementioned natural components within the pharmaceutical compositions are oils that comprise rich sources of essential fatty acids (e.g., behenic acid, oleic acid, and lauric acid); one or more skin lipids; and a butter including linoleic acid and linolenic acid.

In some embodiments, the synergistic effect provided by the combination of pracaxi oil and seje oil increases the skin permeability to the APIs thereby passing through the stratum corneum and reaching the target area. In these embodiments, the increased skin permeability is due to the oil's high concentrations of oleic, linolenic, linoleic acids and sterols, such as beta-sitosterol and stigmasterol; and phosphatidylcholine. Further to these embodiments, the aforementioned natural components within the pharmaceutical compositions act synergistically to increase the skin permeation of water and oil soluble products. In other embodiments, when the pharmaceutical compositions are prepared, liposomes formed from the fatty acids, including behenic acid and oleic acid that are present on one or more oils, and are stabilized by the phospholipids within the pharmaceutical compositions.

In an example, the pharmaceutical compositions include: pracaxi oil in amounts ranging from about 0.5% w/w to about 15% w/w, preferably from about 1% w/w to about 5% w/w; seje oil in amounts ranging from about 0.5% w/w to about 15% w/w, preferably from about 1% w/w to about 5% w/w; phosphatidylcholine in amounts ranging from about 0.1% w/w to about 5% w/w, preferably from about 0.5% w/w to about 2% w/w; and silicone in amounts ranging from about 10% w/w to about 95% w/w, preferably from about 10% w/w to about 50% w/w.

In other embodiments, the pharmaceutical compositions include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. Further to these embodiments, the concentration of each natural component within pharmaceutical compositions is from about 1% w/w to 20% w/w, more preferably about 5% w/w.

In further embodiments, the pharmaceutical compositions can be applied alone or as a carrier for APIs (e.g., antibiotics, anti-fungal, cortical steroids, non-steroidal anti-inflammatories, anti-parasites, and the like).

In some embodiments, example active pharmaceutical ingredients (APIs) for use within the pharmaceutical compositions as antibiotics include aminoglycosides, amikacin, gentamicin, kanamycin, neomycin, netilmicin, tobramycin, paromomycin, spectinomycin, ansamycins, geldanamycin, herbimycin, rifaximin, carbacephem, loracarbef, carbapenems, ertapenem, doripenem, meropenem, cephalosporins, cefadroxil, cefazolin, cefalotin, cefalexin, cephalosporins, cefaclor, cefamandole, cefoxitin, cefprozil, cefuroxime, cephalosporins, cefixime, cefdinir, cefditoren, cefoperazone, cefotaxime, cefpodoxime, ceftazidime, ceftibuten, ceftizoxime, ceftriaxone, cephalosporins, cefepime, cephalosporins, ceftaroline fosamil, ceftobiprole, glycopeptides, teicoplanin, vancomycin, telavancin, lincosamides, clindamycin, lincomycin, lipopeptide, daptomycin, macrolides, azithromycin, clarithromycin, dirithromycin, erythromycin, roxithromycin, troleandomycin, telithromycin, spiramycin, monobactams, aztreonam, nitrofurans, furazolidone, nitrofurantoin, oxazolidonones, linezolid, posizolid, radezolid, torezolid, penicillins, amoxicillin, ampicillin, azlocillin, carbenicillin, cloxacillin, dicloxacillin, flucloxacillin, mezlocillin, methicillin, nafcillin, oxacillin, penicillin, piperacillin, temocillin, ticarcillin, polypeptides, bacitracin, colistin, polymyxin b, quinolones, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, sulfonamides, mafenide, sulfadiazine, sulfamethizole, sulfamethoxazole, sulfanilimide (archaic), sulfasalazine, sulfisoxazole, tetracyclines, demeclocycline, doxycycline, minocycline, oxytetracycline, tetracycline, clofazimine, dapsone, capreomycin, cycloserine, ethambutol, ethionamide, isoniazid, pyrazinamide, rifabutin, rifapentine, streptomycin, arsphenamine, chloramphenicol, fosfomycin, metronidazole, mupirocin, quinupristin/dalfopristin, thiamphenicol, tigecycline, trimethoprim, and combinations thereof, among others.

In other embodiments, example APIs for use within the pharmaceutical compositions as suitable antifungals include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof, among others.

In further embodiments, example APIs for use within the pharmaceutical compositions as antivirals include acyclovir, famciclovir and valacyclovir. Other antiviral agents include abacavir, aciclovir, adefovir, amantadine, amprenavir, arbidol., atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, immunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof, among others.

In some embodiments, example APIs for use within the pharmaceutical compositions as cortical steroids include hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone, among others.

In other embodiments, example APIs for use within the pharmaceutical compositions as anti-parasites include amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof, among others.

Pracaxi Oil

Pracaxi oil is obtained from the seed oil of the *Pentaclethara macroloba* tree, or pracaxi tree. The pracaxi tree is a deciduous tree from the legumes family, growing in altitudes below about 600 meters in many parts of northern Brazil, Guyana, Trinidad, and parts of Central America, and may reach between about 8 and about 35 meters in height. Pracaxi trees may sometimes be found in wetlands, and are resistant to water logging.

Pracaxi seeds include from 45% to 48% fat, 27% to 28% protein, and 12% to 14% carbohydrates (see Table 1). Pracaxi seed oil includes the highest known natural concentration of behenic acid (about 20%) in a vegetable fat, more than six times higher than in peanut oil, and also includes about 35% of oleic acid. In some cases, pracaxi seed oil may include greater percentages of the aforementioned behenic acid and oleic acid. The oleic acid and lauric acid, contained within pracaxi oil are effective vehicles at delivering drugs through the skin.

TABLE 1

General composition of pracaxi oil.

| Components | Composition % |
|---|---|
| Fat | 45-48 |
| Protein | 27-28 |
| Carbohydrates | 12-14 |

An exemplary fatty acid composition of pracaxi oil is illustrated below in Table 2. Compositions vary depending on the region and conditions in which the pracaxi tree grows.

TABLE 2

Exemplary fatty acid composition of pracaxi oil.

| Fatty Acids | Carbon Atoms | Composition % |
|---|---|---|
| Lauric | 12:00 | 1.30 |
| Myristic | 14:00 | 1.21 |
| Palmitic | 16:00 | 2.04 |
| Stearic | 18:00 | 2.14 |
| Oleic | 18:10 | 44.32 |
| Linoleic | 18:20 | 1.96 |
| Linolenic | 18:30 | 2.31 |
| Behenic | 22:00 | 9.67 |
| Lignoceric | 24:00 | 14.81 |

TABLE 3

Specifications of pracaxi oil.

| Indicators | Reference Value |
|---|---|
| Texture | Solid below 18.5° C., liquid viscous texture above this temperature |
| Color | Translucent yellow, yellowish-white when solid |
| Odor | Almost odorless |
| Melting point | 18.5° C. |
| Refractive index (40° C.) | 1.4690 |
| Iodine value | 65-70 g I2/100 g |
| Saponification value | 170-180 mg kOH/g |
| Acid value | 3-5 mg KOH/g |
| Peroxide value | 5-10 mEQ/kg |
| Density (25°) | 0.917 g/cm$^3$ |

Pracaxi oil has been widely employed for its cosmetic, therapeutic, and medicinal properties. Pracaxi oil is rich in organic acids with antioxidant, antibacterial, antiviral, antiseptic, antifungal, anti-parasitic, and anti-hemorrhagic properties. Because pracaxi oil possesses many of the aforementioned properties, pracaxi oil can be suitable oil for helping in the treatment of ear diseases.

Pracaxi oil has a high amount of solid matter, not fatty acids, which make pracaxi oil solidifies in cooler temperatures. The solid matter has gentle moisturizing and high cellular renewal promoting properties. It includes vitamin E, and has essential fatty acids, which makes pracaxi oil suitable oil for pharmaceutical compositions.

Pataua Oil

Pataua oil, also called seje oil, is extracted from the mesocarp of the patauá palm and generally appears as a greenish-yellow and transparent liquid, with little odor and taste, having the physical appearance and composition of fatty acids that are similar to olive oil (*Olea europaea*). Pataua oil has a high content of unsaturated fatty acids. Pataua oil also has a high content of oleic acid, which allows pataua oil to be used as skin moisturizer. The dry mesocarp of patauá palm includes about 7.4% protein and possesses an excellent amino acid composition. Because of this, the protein of patauá is one of the most valuable found among plants and may be compared with the meat or milk from cattle. The most abundant sterols found within pataua oil are $\Delta^5$avenosterol and β-sitosterol, with relative contents of about 35% and about 38%, respectively. The most abundant aliphatic alcohols found within pataua oil are those with 7, 8, and 10 carbon atoms. Among tocopherols found within pataua oil, α-tocopherol was predominant. Aldehydes such as heptanal, octanal and decanal were present in the volatile fraction of pataua oil along with terpenoid compounds.

TABLE 4

Fatty acid composition of pataua oil.

| Fatty Acids | Carbon Atoms | Composition % |
|---|---|---|
| Palmitic | 16:00 | 13.2 |
| Palmitoleic | 16:10 | — |
| Stearic | 18:00 | 3.6 |
| Oleic | 18:10 | 77.7 |
| Linoleic | 18:20 | 2.7 |
| Linolenic | 18:30 | 0.6 |
| Arachidic | 20:00 | 2 |
| Unsaturated | | 81.6 |

Administration

In some embodiments, when an affected area is not reachable because of the inflammation caused by ear diseases, the application of disclosed pharmaceutical compositions reduces the inflammation and opens up the ear canal to enable for other pharmaceutical compositions including any suitable APIs or the pharmaceutical compositions by themselves to be applied directly into the affected area.

In some embodiments, the amounts of the natural components within the pharmaceutical compositions are combined to produce a single dosage form. In these embodiments, the pharmaceutical compositions dosage forms include: sprays, ointments, pastes, creams, lotions, solutions, topical gels, patches, among others. In these embodiments, the pharmaceutical compositions enable for continuous treatment of ear diseases by applying one layer of disclosed pharmaceutical compositions into the affected area of a patient.

In some embodiments, the pharmaceutical compositions are directly administered into the affected area. In these embodiments, suitable applicators are employed to administer the pharmaceutical compositions. In an example, suitable applicators include a swab, brush, cloth, pad, and sponge, among others.

In other embodiments, the pharmaceutical compositions are prepared to deliver a specific dosage of APIs. In these embodiments, the dosage is dependent on the patient to whom the pharmaceutical compositions are being administered.

In an example, the pharmaceutical compositions are employed for treating cauliflower ear by administering the pharmaceutical compositions to the affected tissue. In this example, the pharmaceutical compositions are administered inside the outer ear, thereby increasing the penetration of the APIs into the affected area, as well as the residence time of the compositions at the targeted site. Further to this example, the pharmaceutical compositions are administered directly into the affected tissue, twice a day (between about 2 g to about 6 g) from about 2 weeks to about 10 weeks. In this example, the results are observed within the first week of treatment.

In some embodiments, pharmaceutical compositions exhibit increased permeability; therefore, the dosage and time of treatment is significantly reduced.

In another example, the pharmaceutical composition is an otic pharmaceutical gel. In this example, the otic pharmaceutical gel is employed for treating an infection within a canine's internal ear.

Figure 2:
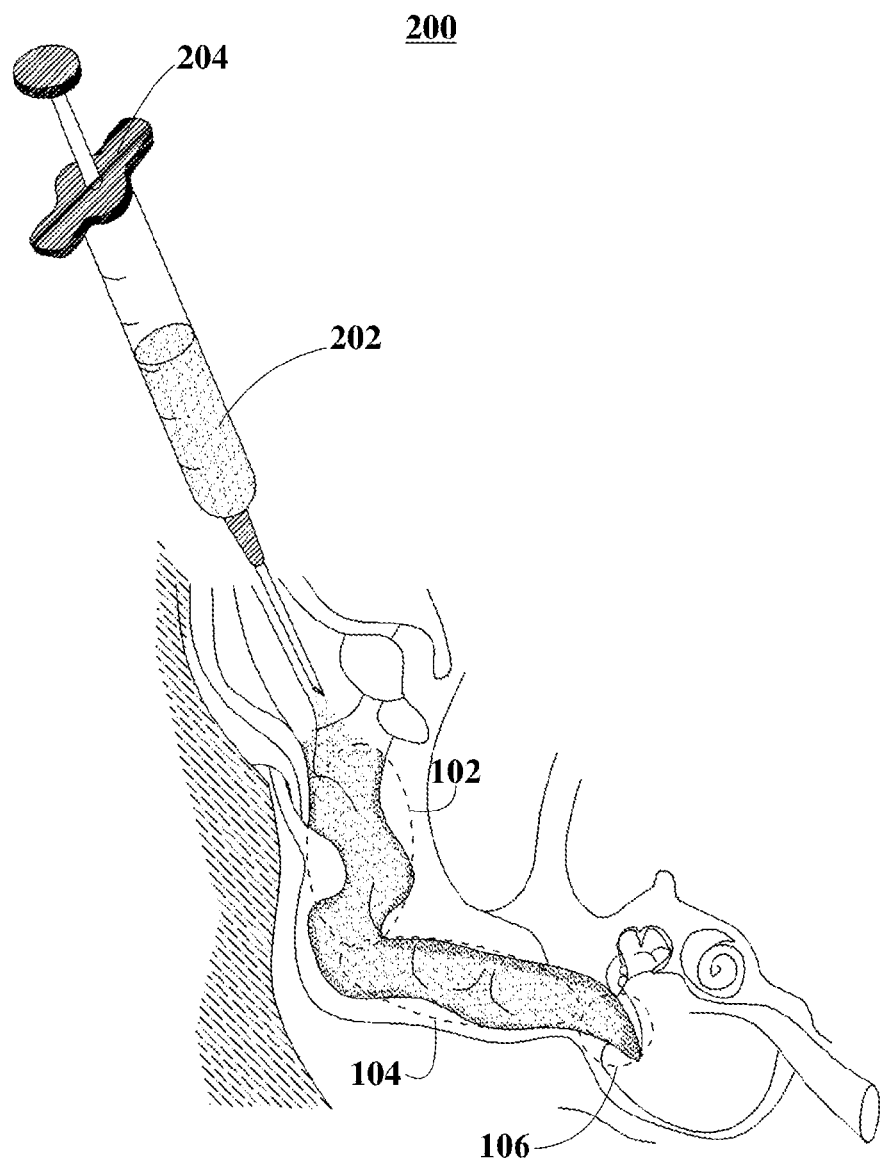
FIG. 2 is a graphical representation illustrating the application of an otic pharmaceutical gel into an infected area of a canine's internal ear, according to an embodiment.

FIG. 2 is a graphical representation illustrating the application of an otic pharmaceutical gel into an infected area of a canine's internal ear. In FIG. 2, administration technique 200 illustrates otic pharmaceutical gel 202, delivery device 204, vertical canal 102, horizontal canal 104, and tympanic membrane 106. In FIG. 2, elements having identical element numbers from previous figures perform in a substantially similar manner.

In some embodiments, otic pharmaceutical gel 202 is applied into the affected area. In these embodiments, the dosage of otic pharmaceutical gel 202 varies according to the animal size or weight. In an example, small animals need amounts ranging from about 0.5 mL to 1.5 mL of otic pharmaceutical gel 202. In another example, animals over 100 pounds need amounts ranging from about 4 mL to 9 mL of otic pharmaceutical gel 202 in the infected ear. Further to these embodiments, otic pharmaceutical gel 202 is applied by employing calibrated delivery device 204. In these embodiments, calibrated delivery device 204 is sterilized prior to its use. In some circumstances (e.g., perforated tympanic membrane), sterilization is mandatory.

In some embodiments, otic pharmaceutical gel 202 is instilled by employing calibrated delivery device 204 through vertical canal 102 in order to reach the horizontal canal 104, without puncturing tympanic membrane 106. In these embodiments, the otic pharmaceutical gel reaches the affected area. In an example, otic pharmaceutical gel 202 is instilled once, and a single dose is enough to observe healing within the next 7 days. In another example, otic pharmaceutical gel 202 is applied twice a day.

In some embodiments, various additives are included to facilitate the preparation of suitable dosage forms. For example, additives include gelling agents, thickening agents, pH adjusters, preservatives, colors, stabilizing agents, antioxidants, and surfactants, among others.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method of treating an aural hematoma comprising:
    applying a first pharmaceutical composition, including
        pracaxi oil,
        seje oil,
        silicone, and
        an effective amount of at least one first active pharmaceutical ingredient, to an ear having the aural hematoma wherein applying the first pharmaceutical composition is configured to reduce inflammation and provide access to an infected site and
    applying a second pharmaceutical composition including at least one second active pharmaceutical ingredient to the infected site wherein applying the second pharmaceutical composition is configured to treat an infection at the infected site.

2. The method of treating an aural hematoma of claim 1, wherein the first pharmaceutical composition comprises
    about 0.5% w/w to about 15% w/w pracaxi oil,
    about 0.5% w/w to about 15% w/w seje oil, and
    about 10% w/w to about 95% w/w silicone.

3. The method of treating an aural hematoma of claim 2, wherein the first pharmaceutical composition further comprises about 0.1% w/w to about 5% w/w phosphatidylcholine.

4. The method of treating an aural hematoma of claim 3, wherein the first pharmaceutical composition comprises about 0.5% w/w to about 2% w/w phosphatidylcholine.

5. The method of treating an aural hematoma of claim 2, wherein the first pharmaceutical composition comprises about 10% w/w to about 50% w/w silicone.

6. The method of treating an aural hematoma of claim 3, wherein the first pharmaceutical composition comprises about 10% w/w to about 50% w/w silicone.

7. The method of treating an aural hematoma of claim 6, wherein the first pharmaceutical composition comprises about 1% w/w to about 5% w/w pracaxi oil.

8. The method of treating an aural hematoma of claim 6, wherein the first pharmaceutical composition comprises about 1% w/w to about 5% w/w of seje oil.

9. The method of treating an aural hematoma of claim 6, wherein the first pharmaceutical composition further comprises at least one natural component selected from the group consisting of buriti oil, copaiba balsam, bacaba oil, acai oil, ojon oil, andiroba oil, murumuru butter, and tucuma oil.

10. The method of treating an aural hematoma of claim 9, wherein the first pharmaceutical composition comprises at least one natural component selected from the group consisting of about 1% w/w to about 20% w/w buriti oil, about 1% w/w to about 20% w/w copaiba balsam, about 1% w/w to about 20% w/w bacaba oil, about 1% w/w to about 20% w/w acai oil, about 1% w/w to about 20% w/w ojon oil, about 1% w/w to about 20% w/w andiroba oil, about 1% w/w to about 20% w/w murumuru butter, and about 1% w/w to about 20% w/w tucuma oil.

11. The method of treating an aural hematoma of claim 9, wherein the first pharmaceutical composition comprises at least one natural component selected from the group consisting of about 5% w/w buriti oil, about 5% w/w copaiba balsam, about 5% w/w bacaba oil, about 5% w/w acai oil, about 5% w/w ojon oil, about 5% w/w andiroba oil, about 5% w/w murumuru butter, and about 5% w/w tucuma oil.

12. The method of treating an aural hematoma of claim 10, wherein the first pharmaceutical composition is selected from the group consisting of a spray, an ointment, a paste, a cream, a lotion, a solution, a topical gel, and a patch and wherein at least one layer of the first pharmaceutical composition is applied to the area of the ear to reduce inflammation and provide access for the second pharmaceutical composition to be applied to the infected site.

* * * * *